United States Patent [19]

Benkó et al.

[11] Patent Number: 5,126,457
[45] Date of Patent: Jun. 30, 1992

[54] PROCESS FOR THE PREPARATION OF 1,4-DIHYDRO-PYRIDINE DERIVATIVES

[75] Inventors: Pál Benkó; Dániel Bózsing; László Lévai; Györgyi Koványi née Lax; György Mikite; Péter Tömpe; Éva Furdyga; Ilona Dinnyés née Nagy; Éva Póczik; Györgyi Zalavári née Dósa; Iván Beck; István Simonyi; Kálmán Nagy; János Imre; Erzsébet Kiss née Bertók; Éva J. Tajthy née Juhász; Attila Mándi; Frigyes Görgényi, all of Budapest, Hungary

[73] Assignee: Egis Gyogyszergyar, Budapest, Hungary

[21] Appl. No.: 321,293

[22] Filed: Mar. 8, 1989

[30] Foreign Application Priority Data

Mar. 8, 1988 [HU] Hungary .............................. 1111/88
Mar. 8, 1988 [HU] Hungary .............................. 1112/88
Aug. 2, 1988 [HU] Hungary .............................. 4055/88

[51] Int. Cl.⁵ .......................................... C07D 211/02
[52] U.S. Cl. ..................................... 546/249; 546/321
[58] Field of Search ............................... 546/250, 249

[56] References Cited

PUBLICATIONS

Fox et al., *J. Org. Chem.* 16, 1259 (1951).
Smith, P. *Chemistry of Open–Chain Organic Nitrogen Compounds*, vol. I, W. A. Benjamin Inc., N.Y. (1965), pp. 298–299.

*Primary Examiner*—Joseph P. Brust
*Attorney, Agent, or Firm*—Keil & Weinkauf

[57] ABSTRACT

The invention is directed to processes for the preparation of dimethyl-1,4-dihydro-2,6-dimethyl-4-(2'-nitrophenyl)-pyridine-3,5-dicarboxylate by reacting 1-methoxy-1-(2'-nitrophenyl)-N-(2'-nitrophenyl)methylene methanamie or 1-(2'-nitrophenyl)-N,N'-bis-(2'-nitrophenyl) methylene methanediamine with methyl acetoacetate in the presence of an amine compound or by reacting the monomeric or trimeric from of 2-nitrobenzaldimine with methyl acetoacetate.

16 Claims, No Drawings

PROCESS FOR THE PREPARATION OF 1,4-DIHYDRO-PYRIDINE DERIVATIVES

This invention relates to a new and improved process for the preparation of a 1,4-dihydro-pyridine derivative, to new intermediates useful in the preparation thereof and to a process for the preparation of the said new intermediates.

More particularly, the invention is concerned with new and improved processes for the preparation of dimethyl-1,4-dihydro-2,6-dimethyl-4-(2'-nitrophenyl)-pyridine-3,5-dicarboxylate of the Formula I

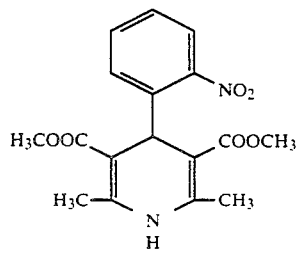

(I)

(referred to further on as "nifedipine").

It is known that nifedipine is a valuable calcium antagonist, which is widely used in the treatment of hypertension of all kinds and of heart muscle diseases (U.S. Pat. No. 3,485,847).

Several methods are known for the preparation of nifedipine. A. Hantzsch [Justus Liebigs Annalen der Chemie 215, 1 (1882)] described a general method for the preparation of 1,4-dihydro-pyridine derivatives by reacting an aldehyde with a 3-keto-carboxylic acid ester in the presence of an excess of ammonia. The reaction is illustrated in reaction scheme A.

reaction scheme A $R-CHO + 2 R_1-CO-CH_2-COOR_2 + NH_3$ (excess) $\longrightarrow$

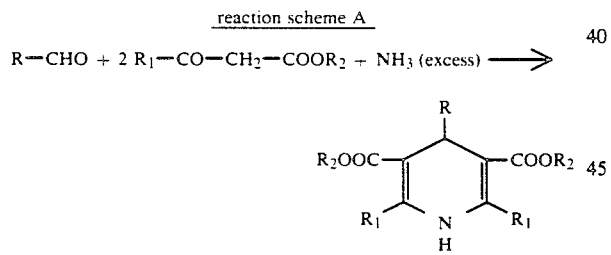

A further general process of A. Hantzsch-Beyer [C. Beyer, Ber. Dtsch. Chem. Ges. 24, 1662 (1891)] is shown in reaction scheme B.

reaction scheme B $R-CHO + 2 R_1-\underset{NH_2}{\overset{}{C}}=CH-COOR_2 \longrightarrow$

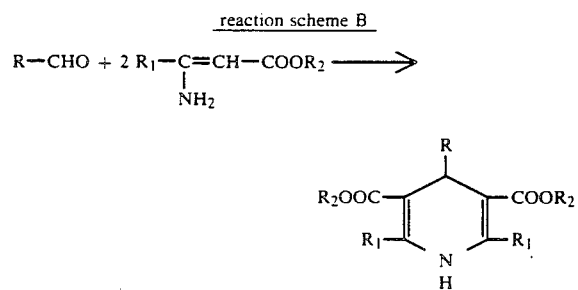

According to this process an aldehyde is reacted with two equivalents of an enamino-carboxylic acid ester. E. Knoevenagel [Ber. Dtsch. Chem. Ges. 31, 743 (1898)] described the reaction of ylidene carboxylic acid esters and enamino carboxylic acid esters. This reaction is illustrated in reaction scheme C.

reaction scheme C

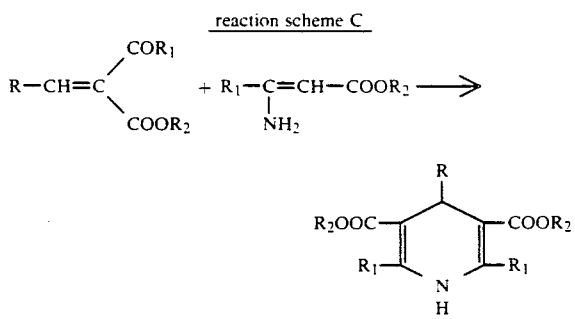

H. H. Fox et al. [J. Org. Chem. 16, 1259 (1951)] studied the reaction of aldehydes, 3-keto-carboxylic acid esters and enamino carboxylic acid esters. The reaction is shown in reaction scheme D.

reaction scheme D $R-CHO + R_1-CO-CH_2-COOR_2 +$

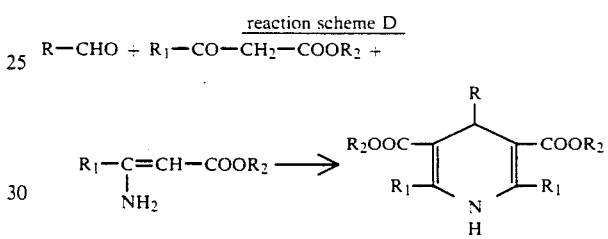

According to DOS No. 2,117,571 dihydro-pyridines are prepared by reacting a nitro-phenyl-benzylidene-acetoacetate with a β-amino-crotonic acid ester or with ammonia and an acetoacetate. The reaction is illustrated in reaction scheme E.

reaction scheme E

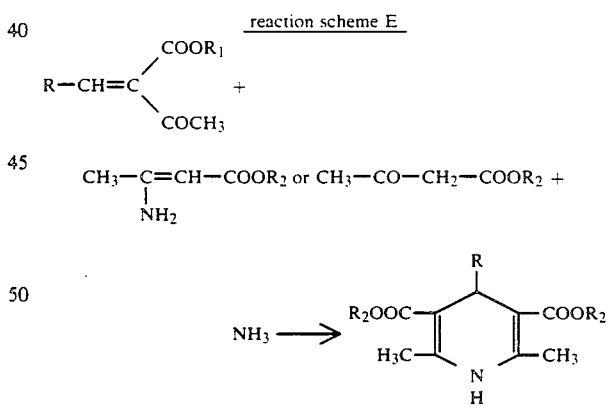

The above methods were applied for the preparation of nifedipine. Thus, according to German patent No. 1,620,827 nifedipine is prepared by reacting 2-nitro-benzaldehyde with methyl acetoacetate in methanol in the presence of an excess of ammonia. The process yields, however, red-brown nifedipine contaminated by numerous by-products. Hungarian patent No. 192,546 contains a critical evaluation of this process and it is disclosed herein that on reproducing Example 1 of German patent No. 1,620,827 nifedipine contaminated by seven by-products is obtained.

Hungarian patent No. 192,546 relates to a modified and improved form of the above-mentioned Knoevenagel-synthesis applied to the preparation of symmetrical 1,4-dihydro-pyridine-dicarboxylates, including nifedipine.

In the first step of the synthesis 2-nitro-benzaldehyde is reacted with methyl acetoacetate in the presence of a catalytic amount (0.01-0.7 mole, related to 1 mole of methyl acetoacetate) of piperidine acetate to give methyl-2-nitro-benzylidene-acetoacetate with a high yield of about 97%. This product is reacted after or without isolation with methyl-3-amino-crotonate. The yield of the second step is 87%, the total yield of both steps amounts to 84.4%. According to the disclosure of the cited Hungarian patent the thin layer chromatogram of the nifedipine thus obtained shows no by-products (Merck-type plate coated with kieselgel; developed with a 3:2:5 mixture of chloroform, acetone and petrolether).

In the course of the earlier procedures—particularly in case of the Hantzsch-type synthesis—if free ammonia is present during the complete reaction period undesired reactions may take place and by-products contaminating the end-product may be formed. Since the requirements of Pharmacopoeia against nifedipine are very high and quality standards for drugs are more and more increasing, there is a great demand for the preparation of nifedipine of high purity, free of contaminations.

The industrial scale use of the process disclosed in Hungarian patent No. 192,546 has several drawbacks. From the economical point of view it is unfavourable that the half amount of the ester component used in the reaction is constituted by the expensive methyl-3-amino-crotonate. A further disadvantage is the long overall reaction time. In the first step the reaction time of the formation of the methyl-2-nitro-benzylidene-acetoacetate amounts to 16 hours, while in the second stage the said ylidene compound is converted into nifedipine in a reaction which requires 36 hours. Thus the total reaction time amounts to 52 hours. The methyl-3-amino-crotonate used must be prepared separately and is more expensive.

It is the object of the present invention to provide an economical industrial scale process for the preparation of nifedipine, whereby the reaction time is shortened and a pure product free of contaminations is obtained.

The process of the present invention is suitable for the economical and high yield industrial scale production of nifedipine of high purity.

According to the present invention there is provided a process for the preparation of dimethyl-1,4-dihydro-2,6-dimethyl-4-(2'-nitro-phenyl)-pyridine-3,5-dicarboxylate of the Formula I, which comprises a) reacting a compound of the Formula II

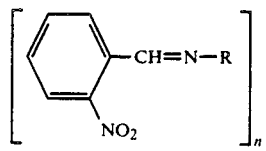
(II)

(wherein n is 1 or 3; if n is 1, then R stands for a group of the Formula (a)

(a)

or (b)

(b)

and if n is 3, then R represents hydrogen) with methyl acetoacetate of the Formula III $CH_3-CO-CH_2-COOCH_3$ (III)

and optionally with an amino compound of the Formula IV

(IV)

(wherein Z is a group of the Formula (c).

$CH_3-\underset{|}{C}=CH-COOCH_3$ (c)

k is 1 and both symbols p are 0; or Z stands for a $C_{1-5}$ straight or branched chain alkanoyloxy group or a carbonate, hydrocarbonate or hydroxy anion, k is 1 and both symbols p are 1; or k is 0, one of both symbols p is 0 and the other is 1) in an inert solvent; or b) reacting 2-nitro-benzaldehyde and methyl acetoacetate of the Formula III and aqueous ammonium hydroxide in the presence of an inert solvent in one step, at a temperature of 101°-120° C., under a pressure of 2.0-6.0 bar.

According to a form of realization of process a) 1-methoxy-1-(2'-nitro-phenyl)-N-(2'-nitro-phenyl)-methylene-methaneamine of the Formula IIA

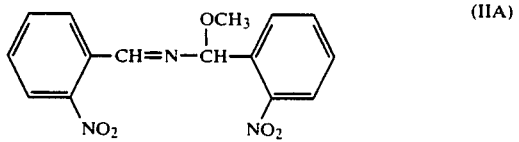
(IIA)

is used as starting material; this is a compound of the Formula II, wherein R is a group of the Formula (a) and n is 1. The reaction is shown in reaction scheme F.

reaction scheme F

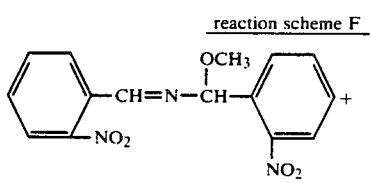
+

$3\ CH_3-CO-CH_2-COOCH_3\ +$ reaction scheme F

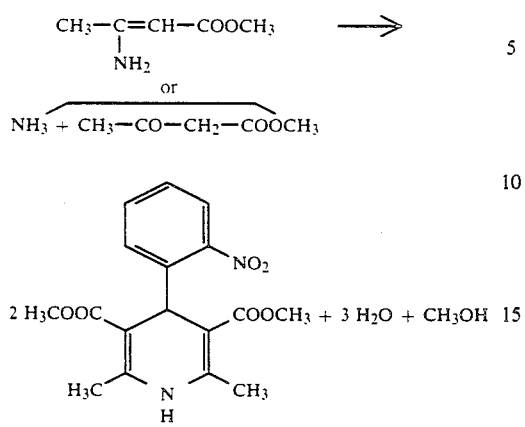

In the course of the reaction 1 mole of the compound of Formula IIA is reacted with 3 moles of methyl acetoacetate and 1 mole of methyl-3-amino-crotonate. The latter component may also be prepared in situ by reacting methyl acetoacetate with ammonia. For this purpose aqueous ammonium hydroxide or methanolic ammonia may be used. The reaction can be carried out in an inert solvent or solvent mixture. As reaction medium any suitable inert solvent may be used which does not interact with the starting materials under the reaction conditions used. Thus, polar protic solvents (e.g. water; alcohols, e.g. methanol, ethanol etc; amides, e.g. formamide, acetamide etc.) or dipolar aprotic solvents (e.g. acetonitrile, acetone, dimethyl sulfoxide, nitrobenzene etc.) may be used. It is very preferred to work in methanol as the medium. The reaction may be accomplished in a broad temperature range, preferably at a temperature between $-10°$ C. and $+120°$ C., advantageously at $5°-100°$ C., particularly at $25°-80°$ C. The reaction time depends on the temperature and may take 12–60 hours, preferably 25–55 hours. The reaction is generally completed within 36 hours with high yields.

One may proceed preferably by adding to a suspension of 1 mole of the compound of the Formula IIA in methanol 3 moles of methyl acetoacetate and subsequently 1 mole of methyl-3-amino-crotonate and heating the reaction mixture to boiling for 36 hours.

One may also proceed by converting the compound of the Formula IIA to nifedipine without isolation in the same apparatus.

The reaction having been completed, nifedipine may be isolated from the reaction mixture by simple methods. The reaction mixture is cooled, the precipitated nifedipine filtered off, dissolved in warm acetic acid, precipitated with water, washed and dried. The product meets the requirements of Pharmacopoeia and no recrystallization is required.

According to a further form of realization of process a) as starting material 1-(2'-nitro-phenyl)-N,N'-bis-(2'-nitro-phenyl)-methylene-methanediamine of the Formula IIB is used. This is a compound of the Formula II, wherein n is 1 and R is a group of the Formula (b). The reaction is illustrated in reaction scheme G.

reaction scheme G

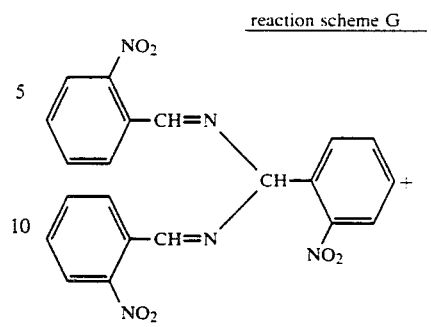

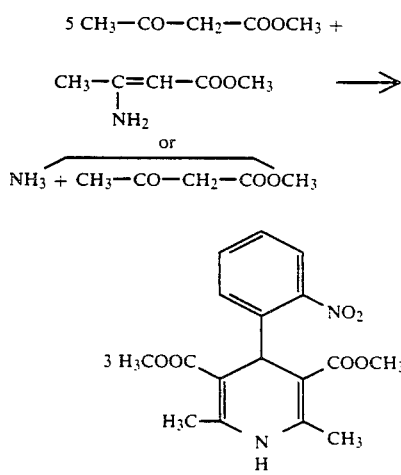

In the course of the reaction 1 mole of the compound of the Formula IIB

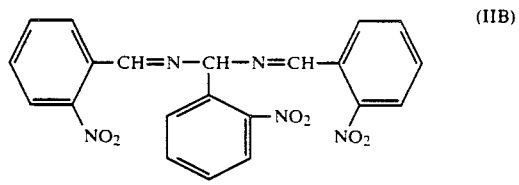

(IIB)

is reacted with 5 moles of methyl acetoacetate and 1 mole of methyl-3-amino-crotonate. This is a compound of the general Formula IV, wherein Z is a group of the Formula (c), k is 1 and both symbols p are 0. The latter component may also be prepared in situ by reacting methyl acetoacetate and ammonia. For this purpose aqueous ammonium hydroxide or methanolic ammonia may be used. The reaction can be carried out in an inert solvent or solvent mixture. As reaction medium any inert solvent which does not interact with the starting material under the reaction conditions may be used. The inert solvents enumerated in connection with the use of the starting material of the Formula IIA may be used. It is particularly preferred to work in methanolic medium. The reaction may be carried out in a broad temperature interval. The reaction temperature may vary between $-10°$ C. and $+120°$ C., preferably at $5°-100°$ C., particularly $25°-80°$ C. The reaction time depends on the temperature and the reaction takes generally 12–60 hours, preferably 25–55 hours. The reaction is generally completed with a high yield within 36–40 hours.

One may also proceed by converting the compound of the Formula IIB to nifedipine without isolation in the same apparatus.

The reaction having been completed, nifedipine may be isolated from the reaction mixture by simple methods. One may preferably proceed by filtering the precipitated nifedipine, washing and drying the product. One may also proceed preferably by dissolving nifedipine in acetic acid under warming and precipitating the product by adding water. The nifedipine thus obtained meets the requirements of Pharmacopoeia and no recrystallization is required.

According to a further form of realization of process a) trimeric 2-nitrobenzaldimine of the Formula IIC

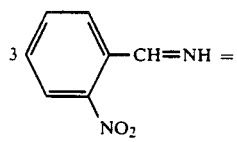 

(IIC)

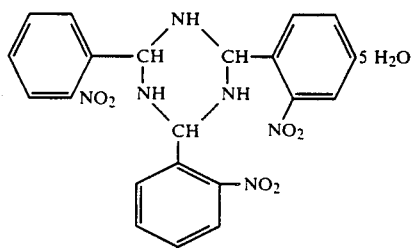

is used as starting material. This compound exists in monomeric form too and is a compound of the general Formula II wherein n is 3 and R stands for hydrogen. The reaction is illustrated in reaction scheme H.

reaction scheme H

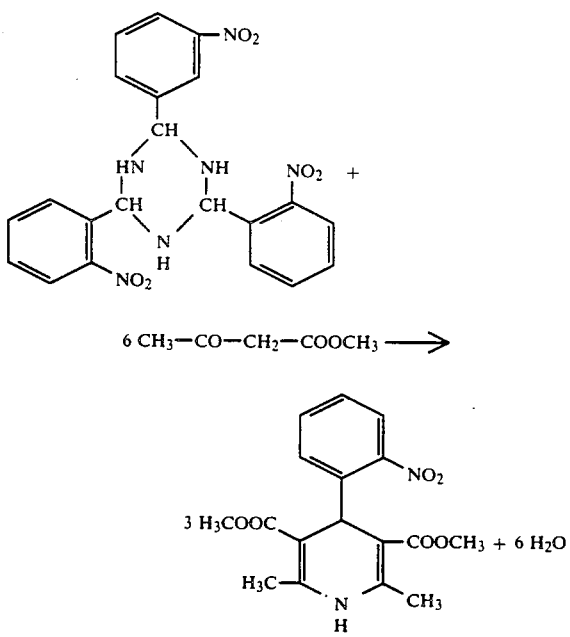

In the course of the reaction 1 mole of a compound of Formula IIC is reacted with 6 moles of methyl acetoacetate. The reaction is carried out in an inert solvent which does not interact with the starting materials under the reaction conditions used. As reaction medium a solvent or solvent mixture enumerated in connection with the use of the starting material of the Formula IIA may be used. One may work particularly advantageously in methanol as medium. The reaction temperature may vary between wide ranges. One may work generally at a temperature between $-10°$ C. and $+120°$ C., preferably at $5°-100°$ C., particularly preferably at $25°-80°$ C. The reaction time depends on the temperature and the reaction takes generally 12-60 hours, preferably 25-55 hours. The particularly preferred reaction time amounts to 36-50 hours.

One may also proceed by converting the compound of the Formula IIC to nifedipine without isolation in the same apparatus.

The nifedipine thus obtained may be isolated from the reaction mixture by simple methods. One may proceed by cooling the reaction mixture, separating the nifedipine by filtration or centrifuging, or dissolving nifedipine in warm acetic acid, precipitating by addition of water, washing and drying. The nifedipine thus obtained meets the requirements of Pharmacopoeia.

The starting materials of the general Formula II are new compounds, not described in prior art.

According to a further aspect of the present invention there is provided a process for the preparation of compounds of the general Formula II, which comprises A) for the preparation of a compound of the Formula II, wherein n is 1 and R stands for a group of the Formula (a), reacting 2-nitro-benzaldehyde with an ammonium salt of the general Formula $R_1$-COONH$_4$ (wherein $R_1$ is hydrogen or $C_{1-4}$ alkyl) and methanol; or B) for the preparation of the compounds of the Formula II, wherein n is 1 and R stands for the group of the Formula (b), reacting 2-nitro-benzaldehyde with an ammonium salt of the Formula $R_1$-COONH$_4$ (wherein $R_1$ is as stated above) or with ammonium hydroxide; or C) for the preparation of the compounds of the Formula II, wherein n is 3 and R stands for hydrogen, reacting 2-nitro-benzaldehyde with ammonia in an inert solvent;

and, if desired, isolating the compound of the Formula II thus obtained from the reaction mixture.

According to the above process A) 2-nitro-benzaldehyde is reacted with an ammonium salt of the Formula $R_1$-COONH$_4$ and methanol. $R_1$ may be a straight or branched chain alkyl group having 1-4 carbon atoms (e.g. methyl, ethyl, n-propyl, isopropyl, n-butyl etc.). As ammonium salt of the Formula $R_1$-COONH$_4$ preferably ammonium acetate may be used. The methanol used as reactant may also be preferably applied in an excess whereby it acts as reaction medium, too. The reaction may be accomplished in a broad temperature range. One may work at a temperature between $-10°$ C. and $+80°$ C., preferably at $15°-40°$ C. The reaction is accomplished within a relatively short time, it takes about 1.5-7 hours. The desired compound of the Formula IIA is obtained with excellent yeilds in a reaction period of about 7 hours.

The reaction may also be carried out in any other inert solvent, which does not interact with the starting materials under the conditions used.

The compound of the Formula IIA thus obtained may be isolated from the reaction mixture by known methods. The product may be very simply isolated by cooling the reaction mixture, filtration or centrifuging and subsequent washing and drying. One may also proceed by converting the compound of the Formula IIA directly, without isolation, to nifedipine in the same apparatus.

According to process B) 2-nitro-benzaldehyde is reacted with an ammonium salt of the Formula $R_1$-COONH$_4$ or ammonium hydroxide. As ammonium salt of the Formula $R_1$-COONH$_4$ preferably ammonium acetate may be used. The reaction of 2-nitro-benzaldehyde and ammonium acetate may be carried out in an inert solvent as medium. For this purpose any inert solvent may be used which does not interact with the starting materials under the reaction conditions used. Thus, preferably polar protic solvents (e.g. water; aliphatic alcohols having at least two carbon atoms, such as ethanol, isopropanol etc.; amides, e.g. formamide, acetamide etc.) or dipolar aprotic solvents (e.g. acetonitrile, acetone, dimethyl sulfoxide, nitrobenzene etc.) may be used. The reaction can be preferably performed in isopropanol as medium.

One may also proceed by reacting 2-nitro-benzaldehyde with ammonium hydroxide. As reaction medium preferably methanol can be used.

The reaction of process B) may be carried out in a broad temperature range. The reaction may be preferably accomplished at a temperature between $-10°$ C. and $+80°$ C., particularly at $15°$-$40°$ C. The reaction takes place within a relatively short period of time and takes generally 6-7 hours. The compound of the Formula IIB is obtained with excellent yields with a reaction time of about 7 hours.

The compound of the Formula IIB thus obtained may be isolated by known and simple methods, e.g. as described in connection with the isolation of the compound of the Formula IIA.

One may also proceed by converting the compound of the Formula IIB to nifedipine without isolation in the same apparatus.

According to process C) 2-nitro-benzaldehyde is reacted in an inert solvent with ammonia. One may proceed preferably by reacting a solution of 2-nitro-benzaldehyde and methanol with a methanolic ammonium solution. The reaction may, however, also be accomplished in any inert solvent which does not interact with the starting materials under the conditions used. Thus the solvents enumerated in connection with the use of the starting material of the Formula IIB (process B) may be used.

The reaction may be performed in a broad temperature interval. One may work at a temperature between $-10°$ C. and $+80°$ C., preferably at $15°$-$40°$ C. The reaction takes generally 5-25 hours.

The compound of the Formula IIC may be isolated by simple methods, e.g. as disclosed in connection with process A). One may also proceed by converting the compound of the Formula IIC to nifedipine without isolation, in the same apparatus.

It has been found that the compounds of the general Formula II may be prepared with excellent yields and in such purity that they can be converted directly without recrystallization to highly pure nifedipine which meets the requirements and quality standards of Pharmacopoeia.

It has been found in a surprising manner that if 2-nitro-benzaldehyde is reacted in the same organic solvent—in methanol—, the structure of the compound of the Formula II formed depends on the character of the ammonia-source used. The relationship between the ammonia source and the structure of the compound of the Formula II obtained is shown in Table I.

TABLE I

| Ammonia source | Structure of product | Yield |
| --- | --- | --- |
| Ammonium acetate | IIA | 98% |
| Ammonium hydroxide | IIB | 92% |
| Anhydrous ammonia | IIC | 75% |

The starting materials used (2-nitro-benzaldehyde, ammonium salts of the Formula $R_1$-COONH$_4$, ammonium hydroxide, methanol) are commercially available products.

According to process b) nifedipine is prepared by reacting 2-nitro-benzaldehyde with methyl acetoacetate of the Formula III and aqueous ammonium hydroxide in the presence of an inert solvent in one step, at a temperature of $101°$-$120°$ C., under a pressure of 2.0-6.0 bar.

It has been found that if 2-nitro-benzaldehyde, methyl acetoacetate and ammonium hydroxide are reacted in the presence of an inert organic solvent under a pressure of 2.0-6.0 bar at a temperature of $101°$-$120°$ C., the reaction takes place in one step very rapidly during a very short time and a pure product is obtained which meets the requirements of Pharmacopoeia without purification.

On the basis of the teaching of the prior art it was not aforeseen and is surprising that reaction with ammonia under pressure at $101°$-$120°$ C. provides a product of such high purity. It has been found in a surprising manner that on raising the temperature to the above interval, the main reaction which leads to the formation of nifedipine takes place with suitable velocity, while the side reactions which result in the formation of by-products do not become more rapid and do not even practically occur during the short reaction time used. It is particularly surprising that in the presence of ammonia by-products of the so-called diamide-and monoamide-structure, respectively, are not formed even if the reaction is accomplished in the presence of a considerable excess of ammonia (2.0 moles).

According to process b) of the process of the present invention preferably 2-4 moles of methyl acetoacetate and 1-3 moles of ammonia (in the form of an aqueous ammonium hydroxide solution) are used, related to 1 mole of 2-nitro-benzaldehyde. One may proceed particularly advantageously by using 2.2-3.5 moles of methyl acetoacetate and 1.04-2.00 moles of aqueous ammonium hydroxide, related to 1 mole of 2-nitro-benzaldehyde. The concentration of the ammonium hydroxide solution may be preferably 20-30% by weight, particularly 25% by weight.

Process b) is a single-step reaction and no methyl-3-amino-crotonate is required. The reaction is accomplished in the presence of an inert organic solvent. It is preferred to use a lower aliphatic alcohol, particularly methanol.

According to a particularly preferred form of realization of process b) a mixture of 2-nitro-benzaldehyde, methyl acetoacetate, an aqueous ammonium hydroxide solution and an inert organic solvent (preferably methanol) is heated to $101°$-$120°$ C. under pressure. One may work under a pressure of 2.0-6.0 bar, particularly 2.0-3.0 bar. The reaction takes place within a very short period of time and takes about 2-5 hours.

The reaction mixture may be worked up in a very simple manner. The reaction taking some hours at $101°$-$120°$ C. having been completed, the reaction mixture is cooled—generally to $0°$-$5°$ C.—, the precipitated nifedipine is isolated by filtration or centrifuging and washed with methanol.

The product thus obtained meets the requirements of Pharmacopoeia and no further purification is required.

The process is highly suitable for industrial scale manufacture.

The advantages of the present invention may be summarized as follows:

PROCESS A

In course of those known methods which are not Hantzsch-type reactions (i.e. if in addition to the $\beta$-ketocarboxylic acid esters more expensive enamino carboxylic acid esters are also used), the said expensive enamino carboxylic acid ester component constitutes exactly one half of the total amount of the ester starting materials used. Thus, according to the process disclosed in Hungarian patent No. 192,546 1 mole of methyl-3-amino-crotonate is used, related to 1 mole of methyl acetoacetate.

On the other hand, according to the process a) of the present invention enamino carboxylic acid esters (methyl-3-amino-crotonate) are used either not at all (in case of the starting material of the Formula IIC) or the amount thereof is only one-sixth of that of the total ester components used (in case of the starting material of the Formula IIB) or but one-fourth of that of the total ester-components used (in case of the starting material of the Formula IIA).

The reaction time is shorter than in case of the process disclosed in Hungarian patent No. 192,546. In the first step of the said known synthesis the formation of the ylidine derivative requires 16 hours, while the starting materials of process a) of the present invention are formed practically quantitatively and more rapidly, within about 7 hours (see particularly reaction schemes G and F). The conversion of the compound of the Formula II to nifedipine requires approximately the same time as the second step of the process set forth in Hungarian patent No. 192,546 (conversion of the ylidene intermediate to nifedipine).

It is surprising and unforeseeable that despite of the complicated reaction-mechanism the new synthesis route according to process a) provides with such excellent yields highly pure nifedipine being suitable for pharmaceutical purpose without further crystallization and purification steps.

PROCESS B one-step reaction;
very short reaction time of some hours;
no methyl-3-amino-crotonate is used;
very high good yields;
high purity.

It is unexpected that under the reaction conditions used ammonia does not induce undersired side-reactions and no by-products of the diamine- or monoamide-structure are formed. The said side-reactions are suppressed even if the reaction is performed in the presence of a large excess of ammonia.

Further details of the present invention are to be found in the Examples without limiting the scope of protection to the said Examples.

EXAMPLE 1

To a suspension of 315.3 g (1 mole) of 1-methoxy-1-(2'-nitro-phenyl)-N-(2'-nitro-phenyl)-methylene-methaneamine and 1 litre of methanol 348.3 g (3 mole) of methyl acetoacetate and thereafter 115.1 g (1 mole) of methyl-3-amino-crotonate are added. The reaction mixture is heated to boiling for 36 hours whereupon it is cooled. The precipitated product is filtered, sucked dry, dissolved in acetic acid under warming and the product is precipitated with water. The product is filtered, washed with methanol and dried. Thus 572 g of nifedipine are obtained, yield 82.6%, m.p.: 172°–174° C.

The product thus obtained is dissolved in chloroform and subjected to thin layer chromatography on HPTLC Kieselgel 60 plates in a bath containing diisopropyl ether for 2 hours. The chromatogram shows no additional (strange) spots.

The starting material can be prepared as follows:

151.1 g (1 mole) of 2-nitro-benzaldehyde are dissolved in 250 ml methanol whereupon 80 g (1.04 mole) of ammonium acetate are added under stirring. The reaction mixture is stirred at 40° C. for 15 minutes and thereafter at room temperature for 7 hours. The reaction mixture is cooled, the precipitated product filtered, washed with water and dried. Thus 154.5 g of 1-methoxy-1-(2'-nitro-phenyl)-N-(2'-nitro-phenyl)-methylene-methaneamine are obtained, yield 98%, m.p.: 117°–118° C.

EXAMPLE 2

31.5 g (0.1 mole) of 1-methoxy-1-(2'-nitro-phenyl)-N-(2'-nitro-phenyl)-methylene-methane-amine are suspended in 100 ml of methanol. 46.45 g (0.4 mole) of methyl acetoacetate are added, whereupon ammonium hydroxide comprising an equivalent amount of ammonia is added dropwise. The reaction mixture is heated to boiling for 14 hours, then cooled. The precipitated product is filtered, washed with cold methanol and water and dried. Thus 49.2 g of nifedipine are obtained, yield 71%, m.p.: 170°–172° C.

EXAMPLE 3

To a mixture of 31.5 g (0.1 mole) of 1-methoxy-1-(2'-nitro-phenyl)-N-(2'-nitro-phenyl)-methylene-methaneamine and 68 ml of methanol first 46.45 g (0.4 mole) of methyl acetoacetate and subsequently a methanolic ammonia solution comprising 1.7 g (0.1 mole) of ammonia are added. The reaction mixture is heated to boiling for 36 hours, then cooled. The precipitated product is filtered, sucked dry, dissolved in acetic acid under warming, precipitated with water, filtered, washed with water and dried. Thus 51.2 g of nifedipine are obtained, yield 74%, m.p.: 171°–175° C.

EXAMPLE 4

To a suspension of 433.4 g (1 mole) of 1-(2'-nitro-phenyl)-N,N'-bis-(2'-nitro-phenyl)-methylene-methanediamine and 1.5 litre of methanol 580.6 g (5 moles) of methyl acetoacetate and 115.1 g (1 mole) of methyl-3-amino-crotonate are added under stirring. The reaction mixture is heated to boiling for 46 hours, then cooled. The precipitated product is filtered, sucked dry, dissolved in acetic acid under warming, precipitated with water, filtered and dried. Thus 810.2 g of nifedipine are obtained, yield 78.5%, m.p.: 173°–174° C.

The starting material can be prepared as follows:

a) To 500 ml of isopropanol first 151.1 g (1 mole) of 2-nitro-benzaldehyde and subsequently 80 g (1.04 mole) of ammonium acetate are added. The reaction mixture is stirred at 40° C. for 15 minutes and then at room temperature for 7 hours. The reaction mixture is cooled, the precipitated product is filtered, washed with water and dried. Thus 141.6 g of 1-(2'-nitro-phenyl)-N,N'-bis-(2'-nitro-phenyl)-methylene-methane-diamine are obtained, yield 98%, m.p.: 124°–127° C.

b) To a solution of 15.1 g (0.1 mole) of 2-nitro-benzaldehyde and 40 ml of methanol under stirring an ammonium hydroxide solution containing 1.7 g (0.1 mole) of ammonia is added. The solution is stirred at room temperature for 25 hours, then cooled, the precipitated product is filtered, washed with methanol and dried. Thus 13.3 g of 1-(2'-nitro-phenyl)-N,N'-bis-(2'-nitro-phenyl)-methylene-methane-diamine are obtained, yield 92%, m.p.: 123°–126° C.

EXAMPLE 5

To a suspension of 43.3 g (0.1 mole) of 1-(2'-nitro-phenyl)-N,N'-bis-(2'-nitro-phenyl)-methylene-methane-diamine and 140 ml of methanol 69.7 g (0.6 mole) of methyl acetoacetate and 8.7 ml of a 25% ammonium hydroxide solution are added under stirring. The reaction mixture is stirred at 45° C. for 42 hours, then cooled. The precipitated product is filtered, dissolved in acetic acid under warming, precipitated with water and dried. Thus 79.0 g of nifedipine are obtained, yield 76%, m.p.: 172°–173° C.

EXAMPLE 6

9 g (0.02 mole) of trimeric 2-nitro-benzaldehyde-imine and 14 g (0.12 mole) of methyl acetoacetate are dissolved in 25 ml of methanol. The reaction mixture is stirred under boiling for 25 hours, then cooled. The precipitated crystals are dissolved in acetic acid under warming, precipitated with water, cooled, filtered, washed with water and methanol and dried. Thus 12.4 g of nifedipine are obtained, yield 60%, m.p.: 170°–173° C.

The starting material can be prepared as follows:

To a solution of 15.1 g (0.1 mole) of 2-nitro-benzaldehyde and 40 ml of methanol a methanolic solution of 1.7 g (0.1 mole) of ammonia is added dropwise under stirring. The reaction mixture is stirred at room temperature for 20 hours, then cooled, the precipitated product is filtered, washed with methanol and dried. Thus 11.3 g of trimeric 2-nitro-benzaldehyde-imine are obtained, yield 75.3%, m.p.: 117°–119° C.

EXAMPLE 7

Into a 1-liter glass reactor 60.4 g (0.4 mole) of 2-nitro-benzaldehyde, 102.1 g (0.88 mole) of methyl acetoacetate, 28.25 g (0.415 mole) of a 25% aqueous ammonium hydroxide solution and 150 ml of methanol are weighed in. The reactor is closed, whereupon the reaction mixture is heated to boiling at a temperature of 101°–103° C. and a pressure of 2.0–2.2 bar for 5 hours. The reaction mixture is cooled to 0°–5° C., the precipitated product is filtered and washed with methanol. Thus 110.5 g of nifedipine are obtained, yield 79.8%, m.p.: 171.5°–175° C.

According to thin layer chromatography no by-products can be detected. TLC is carried out on commercially available Merck thin plates coated with Kieselgel. A 3 : 2 : 5 mixture of chloroform, acetone and petrolether is used to develop the thin layer chromatogram. According to a more up-to-date HPLC analysis (USP XXI, Supplement 3, page 2018; valid as from Jan. 1, 1986) the nifedipine content of the product amounts to 98.39%. The quality of the product complies with the requirements of the above Pharmacopoeia without further purification.

EXAMPLE 8

One proceeds as described in Example 7 except that the reaction is carried out at a temperature of 120° C. and a pressure of 6.0 bar for 3 hours. Thus 110.7 g of nifedipine are obtained, yield 80.0%. M. p.: 172°–175° C. The product complies with the requirements of USP XXI without purification.

EXAMPLE 9

One proceeds as described in Example 7 except that 0.4 mole of 2-nitro-benzaldehyde, 0.8 mole of a 25% aqueous ammonium hydroxide solution and 0.88 mole of methyl acetoacetate are used. Thus 111.4 g of nifedipine are obtained, yield 80.5%. The product complies with the requirements of USP XXI without further purification. M. p.: 172°–175° C.

EXAMPLE 10

One proceeds as described in Example 7 except that 0.4 mole of 2-nitro-benzaldehyde, 0.415 mole of a 25% aqueous ammonium hydroxide solution and 1.40 moles of methyl acetoacetate are used. Thus 112.1 g of nifedipine are obtained, yield 81%, m.p.: 172°–175° C. The product complies with the requirements of USP XXI without further purification.

EXAMPLE 11

Into an enamelled 250 liter autoclave 25 kg (0.165 kmole) of 2-nitro-benzaldehyde, 53 kg (0.456 kmole) of methyl acetoacetate, 16 kg (0.235 kmole) of a 25% aqueous ammonium hydroxide solution and 80 liter of methanol are weighed in. The apparatus is closed and the reaction mixture is stirred at a temperature of 101°–103° C. and a pressure of 2.0–2.2 bar for 5 hours. The reaction mixture is then cooled to 0°–5° C., the precipitated nifedipine is filtered and washed with methanol. Thus 44.4 kg of nifedipine are obtained, yield 77.5%. According to TLC the product is uniform. According to HPLC the nifedipine content amounts to 98.24%. The product complies with the requirements of USP XXI without further purification. M. p.: 171.5°–175° C.

What we claim is:

1. A process for the preparation of dimethyl-1,4-dihydro-2,6-dimethyl-4-(2'-nitro-phenyl)-pyridine-3,5-dicarboxylate of the formula I,

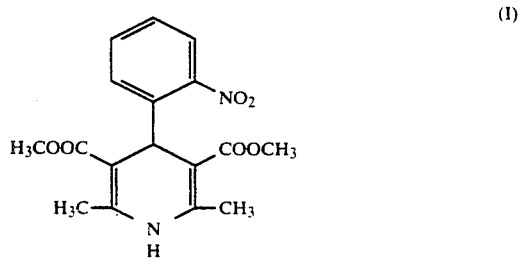

which comprises:
reacting a compound, (II), selected from group consisting of a compound of the formula IIA

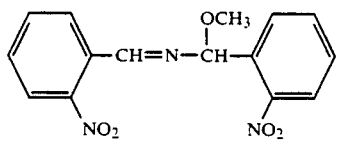 (IIA)

and a compound of the formula IIB

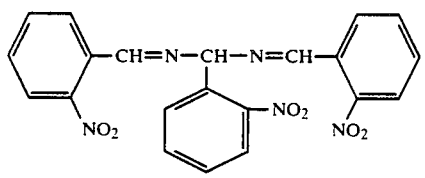 (IIB)

with methyl acetoacetate of the formula III

  CH₃—CO—CH₂—COOCH₃ (III)

and with an amino compound of the formula IV

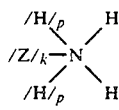 (IV)

(wherein either; Z is a group of the Formula (c),

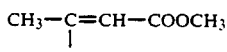 (c)

k is 1 and both symbols p are O; or Z stands for a C₁₋₅ straight or branched chain alkanoyloxy group or a carbonate, hydrocarbonate or hydroxy anion, k is 1 and both symbols p are 1; or k is 0, one of the symbols p is 0 and the other is 1) at a temperature of −10° C. to 120° C. in an inert solvent.

2. The process of claim 1 wherein the compound (II) is of formula IIA.

3. The process of claim 2, which comprises reacting 1 mole of the compound of the formula IIA with 3 moles of methyl acetoacetate (III) and 1 mole of the compound methyl -3-aminocrotonate of the formula IV, wherein Z is a group of the Formula (c), k=1 and both symbols p are O.

4. The process of claim 3, which comprises forming the methyl-3-amino-crotonate in situ by reacting methyl acetoacetate with ammonia.

5. The process of claim 3, which comprises forming the methyl-3-amino-crotonate in situ by reacting methyl acetoacetate with aqueous ammonia hydroxide or methanolic ammonia.

6. The process of claim 2, which comprises reacting a compound of the formula IIA without isolation with methyl acetoacetate and methyl-3-amino-crotonate.

7. The process of claim 2 wherein methanol is used as the inert solvent.

8. The process of claim 1 wherein the compound (II) is of the formula IIB.

9. The process of claim 7, which comprises reacting 1 mole of the compound of the formula IIB with 5 moles of methyl acetoacetate (III) and 1 mole of methyl-3-amino-crotonate of the formula IV. wherein Z is a group of the Formula (c), k is 1 and both symbols p are O.

10. The process of claim 9, which comprises forming methyl-3-amino-crotonate in situ by reacting methylacetoacetate with ammonia.

11. The process of claim 9, which comprises forming methyl-3-amino-crotonate in situ by reacting methylacetoacetate with aqueous ammonium hydroxide or methanolic ammonia.

12. The process of claim 8, which comprises reacting the compound of the formula IIB without isolation with methyl acetoacetate and methyl-3-amino-crotonate.

13. The process of claim 8 wherein a lower aliphatic alcohol is used as the inert solvent.

14. A process for the preparation of dimethyl-1,4-dihydro-2,6-dimethyl-4-(2′-nitro-phenyl)-pyridine-3,5-dicarboxylate of the formula I,

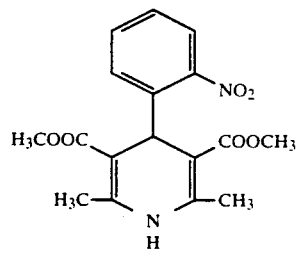 (I)

which comprises:
reacting a compound selected from the group consisting of the monomeric form of the IIC compound

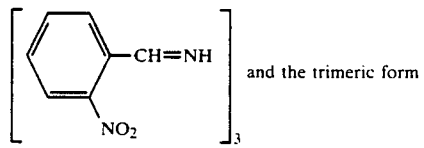 and the trimeric form

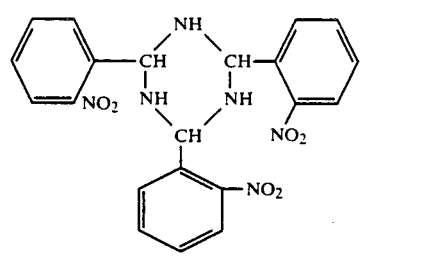 (IIC)

with methylacetoacetate of the formula III

  CH₃—CO—CH₂—COOCH₃ (III)

in an inert solvent at a temperature of −10° C. to 120° C.

15. The process of claim 14 which comprises reacting 1 mole of the compound of formula IIC with 6 moles of methyl acetoacetate.

16. The process of claim 14 wherein methanol is used as the inert solvent.

* * * * *

UNITED STATES PATENT AND TRADEMARK OFFICE
CERTIFICATE OF CORRECTION

PATENT NO. : 5,126,457
DATED : June 30, 1992
INVENTOR(S) : Pal BENKO et al.

It is certified that error appears in the above-identified patent and that said Letters Patent is hereby corrected as shown below:

ON THE TITLE PAGE:
in the Abstract, line 5, delete "methanamie" and insert
-- methanamine --

Signed and Sealed this

Tenth Day of August, 1993

Attest:

MICHAEL K. KIRK

Attesting Officer    Acting Commissioner of Patents and Trademarks